(12) United States Patent
Pratt et al.

(10) Patent No.: US 6,572,532 B1
(45) Date of Patent: Jun. 3, 2003

(54) IMPLANT POSITIONING SYSTEM AND METHOD

(75) Inventors: Clyde Pratt, Somis, CA (US); Robert Schindler, San Francisco, CA (US); Jesse Kramer, San Francisco, CA (US); Roger Carignan, Ventura, CA (US)

(73) Assignee: Advanced Biomedical Devices Inc., San Francisco, CA (US)

( * ) Notice: Subject to any disclaimer, the term of this patent is extended or adjusted under 35 U.S.C. 154(b) by 0 days.

(21) Appl. No.: 09/516,579

(22) Filed: Mar. 1, 2000

Related U.S. Application Data

(60) Provisional application No. 60/122,125, filed on Mar. 1, 1999.

(51) Int. Cl.$^7$ .................................................. A61F 2/02
(52) U.S. Cl. .......................... 600/30; 604/60; 600/102
(58) Field of Search ............................ 604/57, 59–64, 604/164.01–170.03, 272; 600/29, 30, 102, 104–107, 114–115, 121–125, 131

(56) References Cited

U.S. PATENT DOCUMENTS

| | | | | |
|---|---|---|---|---|
| 3,841,334 A | * | 10/1974 | Wolf ..................... | 128/207.29 |
| 4,245,624 A | * | 1/1981 | Komiya | |
| 4,386,602 A | * | 6/1983 | Sheldon et al. ............. | 600/102 |
| 4,773,393 A | * | 9/1988 | Haber et al. | |
| 5,304,147 A | * | 4/1994 | Johnson et al. | |
| 5,336,263 A | * | 8/1994 | Ersek et al. | |
| 5,385,561 A | * | 1/1995 | Cerny | |
| 5,451,406 A | * | 9/1995 | Lawin et al. | |
| 5,588,960 A | * | 12/1996 | Edwards et al. | |
| 5,639,796 A | * | 6/1997 | Lee | |
| 5,700,783 A | * | 12/1997 | Pinto | |
| 5,705,488 A | * | 1/1998 | Janzen et al. | |
| 5,797,835 A | | 8/1998 | Green et al. ................ | 600/106 |
| 5,964,806 A | * | 10/1999 | Cook et al. | |
| 6,053,860 A | * | 4/2000 | Brooks | |
| 6,071,230 A | * | 6/2000 | Henalla | |

* cited by examiner

Primary Examiner—Mark Bockelman
(74) Attorney, Agent, or Firm—Pillsbury Winthrop, LLP

(57) ABSTRACT

The use of implantable bulking materials for the treatment of urinary incontinence and a system for accurate positioning and delivery of bulking materials are described. The implantable materials are biocompatible, non-biodegradable implants which are designed for stabilization in soft tissue through the ingrowth of fibrous tissue after implantation. The positioning and delivery system comprises an injector which is adapted to allow a syringe to be attached and a housing. The housing includes a through cavity adapted to hold a viewing instrument, such as a cystoscope to allow accurate positioning of the injector. The housing also includes one or more injector through cavities, which are adapted to hold the injector at an angle to the viewing instrument. The angle between the viewing instrument and the injector is variably adjustable. The invention embraces the use of the bulking implants with various delivery methods, including the use of the described positioning and delivery system.

17 Claims, 4 Drawing Sheets

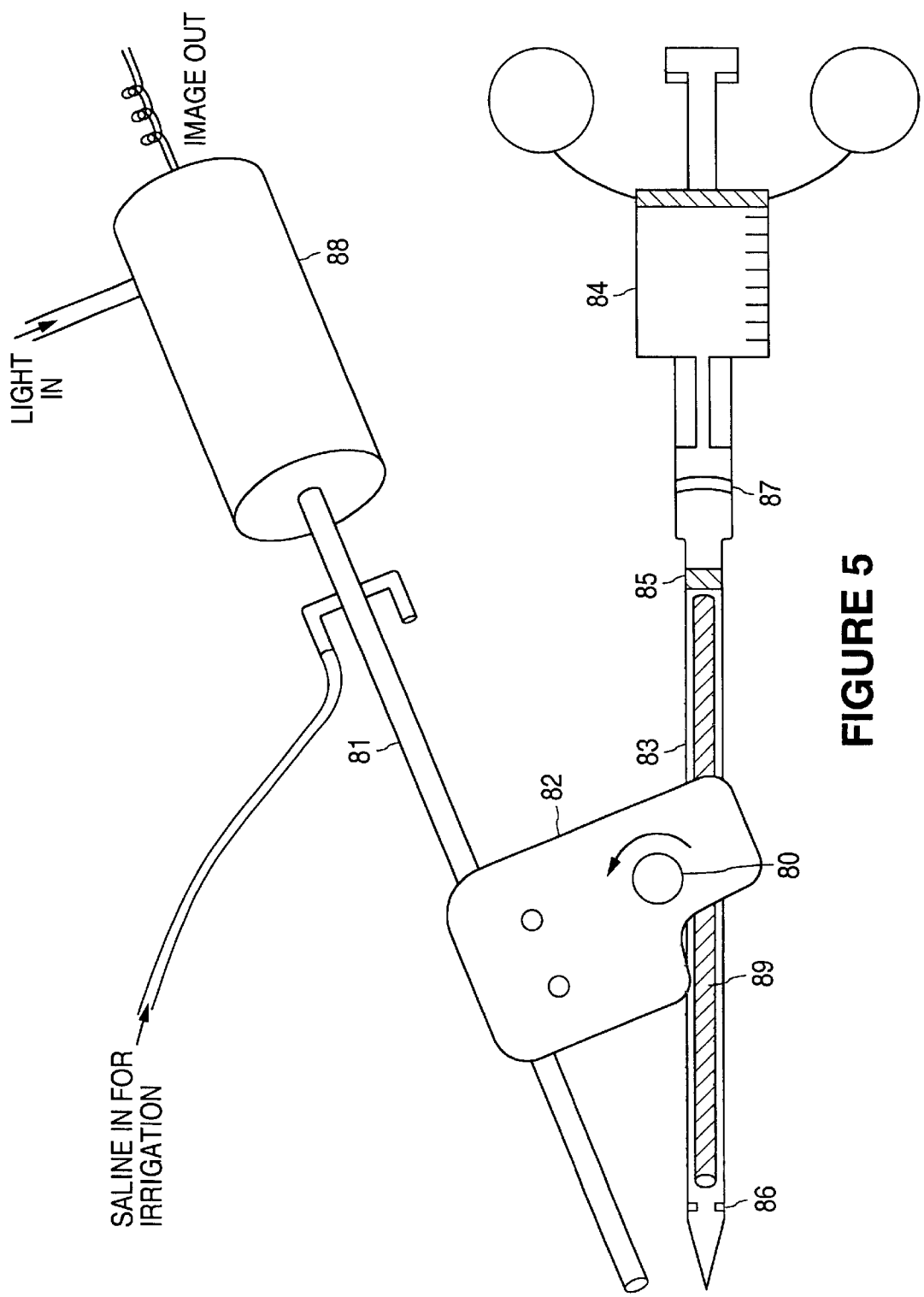

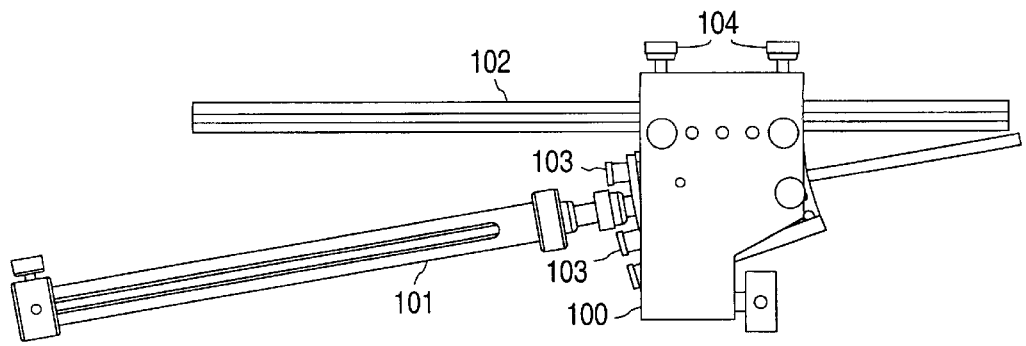
FIGURE 7B
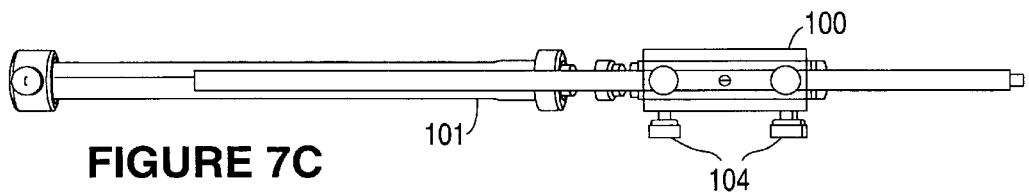
FIGURE 7C
FIGURE 7F
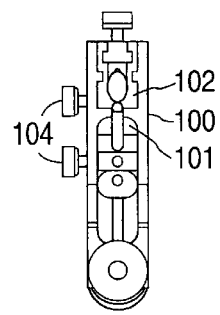
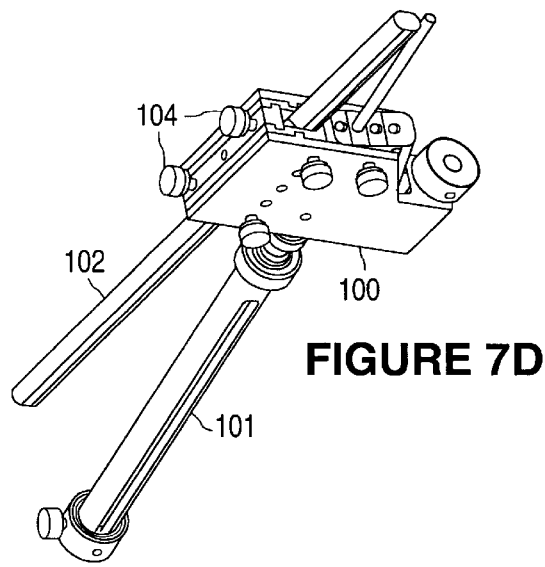
FIGURE 7D
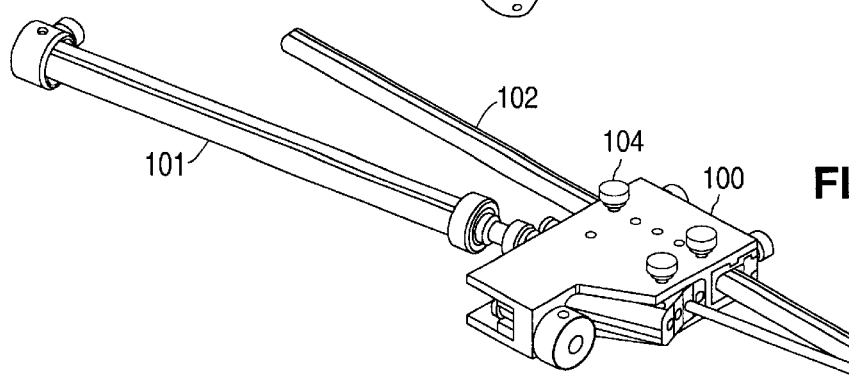
FIGURE 7E

IMPLANT POSITIONING SYSTEM AND METHOD

This application claims benefit of U.S. Application No. 60/122,125 filed on Mar. 1, 1999, which application is incorporated herein by reference.

FIELD OF THE INVENTION

This invention relates to a method and implant for treating urinary incontinence. It further relates to a positioning and delivery system and method for materials that can be implanted in the human body, particularly for the purpose of treating urinary incontinence.

BACKGROUND OF THE INVENTION

Urinary incontinence is an inability to hold urine in the bladder until it is decided to release it. Millions of people, male and female, young and old, experience incontinence. Women are twice as likely to experience incontinence than men are. This is likely due to pregnancy and childbirth, menopause, and the structure of the female urinary tract. However, both men and women can experience incontinence due to strokes, multiple sclerosis, prostate surgery and old age. Urinary incontinence often occurs because of problems in the muscles that hold or release urine, such as sudden contraction of bladder muscles or sudden relaxation of the muscles surrounding the urethra.

There are many types of urinary incontinence—stress incontinence, urge incontinence, functional incontinence, overflow incontinence, transient incontinence, and mixed types of incontinence. Each of these is related to particular physical problems, such as weakened muscles, physical changes, physiological changes, neurological problems, and disease. However, all forms of urinary incontinence are treatable through a variety of surgical and non-surgical procedures.

Among the available non-surgical treatments are Kegel exercises, electrical stimulation of pelvic muscles, biofeedback, timed voiding, bladder training, and medications. Some choose to wear absorbent pads or undergarments. Another choice includes restricting certain liquids. However, each treatment has limited effectiveness and often potentially harmful side effects. For instance, Kegel exercises and electrical stimulation can reduce stress and urge incontinence. Biofeedback may relieve stress and urge incontinence. Medications can reduce certain types of leakage by inhibiting contractions or relaxing muscles. However, these treatments do not cure urinary incontinence. They tend only to alleviate the problem. Further, certain medications can have harmful side effects, such as the increased risk of breast and endometrial cancer associated with estrogen therapy.

Many surgical procedures are also available to treat urinary incontinence. Among the available procedures are pessaries, implants, bladder surgery, and catheterization. Surgical options include surgery to pull the bladder up to a more normal position, surgery to secure the bladder with a wide sling, or surgery to insert an artificial sphincter around the urethra. However, again, each has its own effectiveness rate and possible side effects. For example, one serious concern with the use of pessaries or long-term catheters is urinary tract infections.

Implants into the tissues around the urethra have a partial success rate, but raise concerns of allergic reactions to the implanted material. A commonly used product, Contigen TM, a bovine collagen injectable, can be applied via the perineum, transurethrally or transvaginally. This material provides adequate bulking but only lasts 6–9 months. Teflon (ptfe) paste is currently being explored as a potential bulking agent but has the drawback of consisting of small Teflon particles which may migrate from the position of their original placement in the body.

SUMMARY OF THE INVENTION

The present invention is directed to the use of implantable materials that provide bulking of the periurethral and sphenteric tissues near the bladder neck. The invention is further directed to methods of positioning and delivering such implantable materials. The materials used, and the methods by which they are delivered and positioned, provide a biocompatible implant that directly acts to treat female urinary incontinence. By using biocompatible materials, the body does not reject the implant and the implant provides permanent relocation of tissues in the soft tissue area around the urethra. By using materials of the specified size and shape, the implanted material is designed for the avoidance of migration from its original position in the body. The use of the described positioning and delivery system provides ease in accurately positioning the implant, resulting in better placement for treatment of incontinence.

Overall, the invention provides the ease of use of previous bulking agents, but has the advantage of persistent and more predictable bulking. Additionally, because the material is tubular and non-biodegradable, it is stabilized in soft tissue resulting in less migration.

BRIEF DESCRIPTION OF THE DRAWINGS

The invention will be better understood by reference to the appended figures in which FIG. 5 is a perspective view of a positioning and delivery apparatus;

FIGS. 7A–7F show a further embodiment of the positioning and delivery system from various perspectives;

DETAILED DESCRIPTION OF THE INVENTION

The materials apparatus and methods of the invention are described with respect to the forms of implantable material in FIGS. 1–4 and an apparatus as part of a surgical system for positioning the materials.

Figure 1:
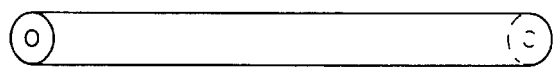
FIG. 1 shows one form of a shaped implantable material according to the present invention
Figure 2:
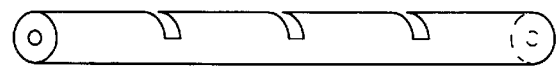
FIGS. 2–4 show additional embodiments of the implantable material of the invention
Figure 3:
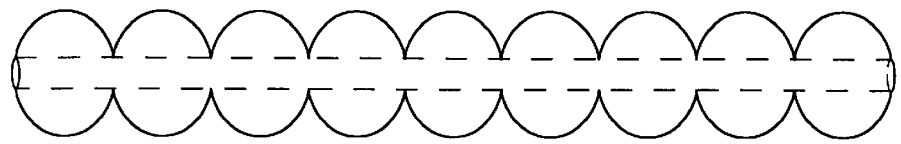
Figure 4:
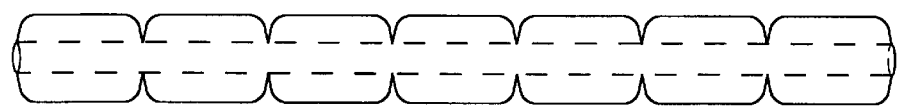

FIG. 1 shows a tube embodiment of the implant. FIG. 2 illustrates a segmented tube embodiment of the implant. FIG. 3 shows a string of conjoined spheres and FIG. 4 shows a string of conjoined cylinders, both in a tubular form, although a solid form may also be used.

In a preferred embodiment the implant of the invention consists of or comprises a series of tubular segments. See, for example, FIG. 2. This implant embodiment is in the form of a single, relatively long tube in which segments have been created. In this preferred form, each segment may measure from about 1 mm to about 20 mm in outside diameter (the outside diameter being selected to obtain the degree of flexibility preferred), and 2 mm to about 30 mm in length. The outside diameter is preferably from 1.5 to 4 mm, with a wall thickness of from about 1 to about 2 mm. The inside diameter of the tubes will preferably be greater than 1 mm. The overall length is between approximately 5 cm and approximately 20 cm. The series of tube segments may be created by radially slitting a longer tube. By slitting the tubes folding points are made and openings are available in the placed implant through which tissue growth can occur. Such growth anchors the tubes to thereby avoid migration, and folding the long tube into implantable segments creates the necessary bulking.

In the case of the single long tube embodiment (see FIG. 1), the basic dimensions would be similar. Slits could still be included to permit tissue in-growth although the implant would not be folded to create latitudinal bulking. Slits are not shown in the embodiment illustrated in FIG. 1 described below. A segmented tube according to the invention is shown in FIG. 2.

Several small, independent tubes could be placed adjacent to one another to provide bulking. In a further embodiment the implant may be made up of a string of small conjoined spheres, shown in FIG. 3, or a string of small conjoined cylinders, shown in FIG. 4. The string of conjoined spheres or conjoined cylinders may be solid or may have a cavity extending through their length. In yet a further embodiment the implant could be a plurality of small spheres. The implant shapes described are exemplary only and are not intended to limit the scope of the invention.

Materials from which the implants of the invention can be formed may preferably be texturally similar to soft tissue and must be biocompatible and non-biodegradable. The materials should be sterilizable and should be able to be formed into the desired shapes. They preferably are porous, i.e. they have a permeable fluid path between the exterior surface and any interior cavity. Such permeability occurs when pores range from 5 to 70 microns. Such pores allow for fluid permeability but do not allow significant tissue ingrowth to occur through the material of the implant. Tissue ingrowth instead occurs because of the tubular or non-smooth shape of the implant. Currently available materials, which may be selected depending on particular circumstances, would include e-PTFE, polyurethane, polyethylene or similar materials. A more preferred form of the implant is a tube, or collection of tubes, a string of small spheres, a string of small cylinders or a collection of spheres each composed of e-PTFE having an internodal distance of from about 10 to about 70 microns.

Methods of bulking using the above-described implants can be implemented using a positioning and delivery system, the elements of which are shown in FIGS. 5–8.

FIG. 5 shows a preferred embodiment of the implant positioning and delivery system which includes a cystoscope or other viewing instrument 81, an adjustable housing 82 for the cystoscope and injector and an injector 83 which includes a plunger 85 and plunger stop 86, a luer lock 87, and a saline solution filled syringe 84, and holds the implant for delivery 89. It also includes a camera 88. In this embodiment, rotatable knob, 80, adjusts the angle between the viewing instrument 81, and the injector, 83.

Figure 6:
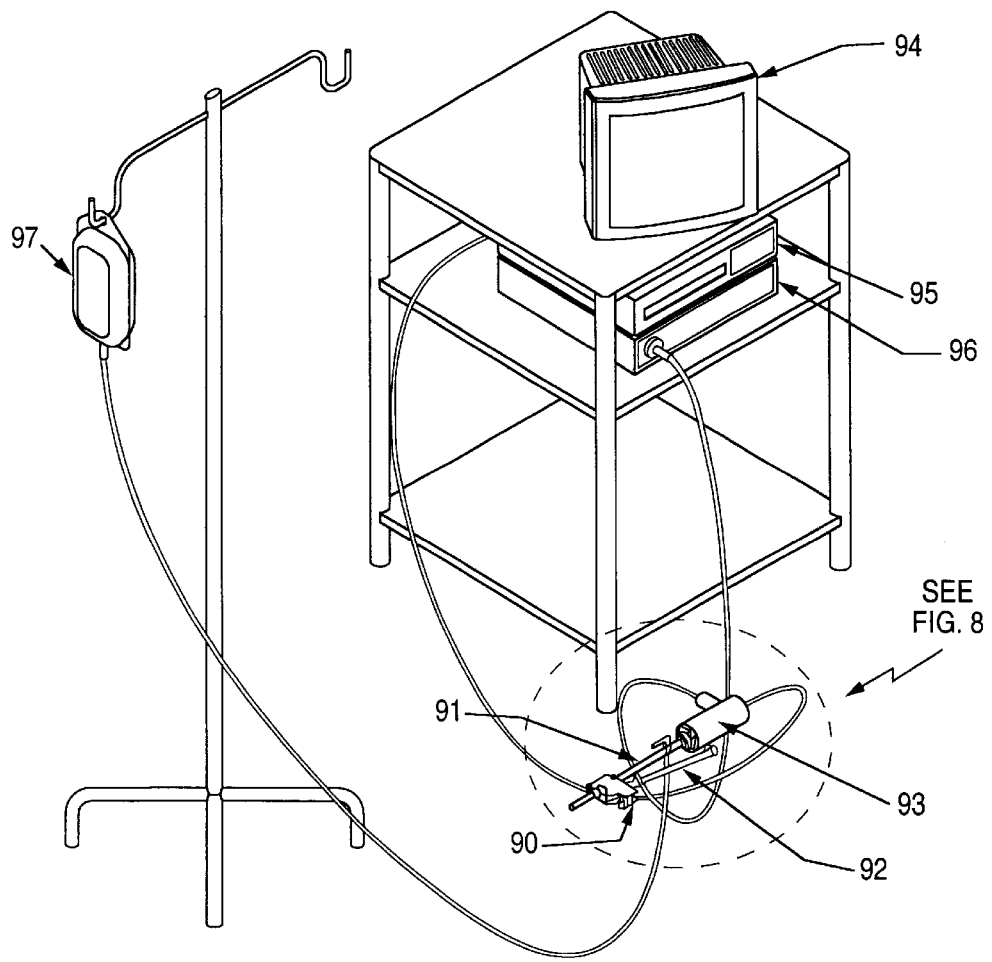
FIG. 6 shows a surgical system including the positioning and delivery.
Figure 7A:
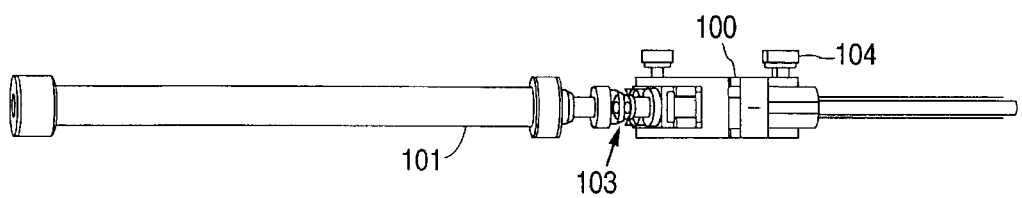

FIG. 6 shows the positioning and delivery system with peripherals for surgical use. The positioning and delivery system includes housing 90, a viewing instrument 91 an injector 92 and a camera 93. The peripherals include a light source 95 and VCR 96, a monitor 94 and a saline solution 97.

FIGS. 7A–7F show various views of one form of a positioning and delivery apparatus. The same number indicating the same element in each view. The positioning and delivery system shown in these figures includes a housing 100, an injector 101 which is inserted in one of several cavities 103 (providing angle selection), a viewing instrument 102 and control knobs 104 for adjustment of the position of the viewing instrument 102.

Figure 8A:
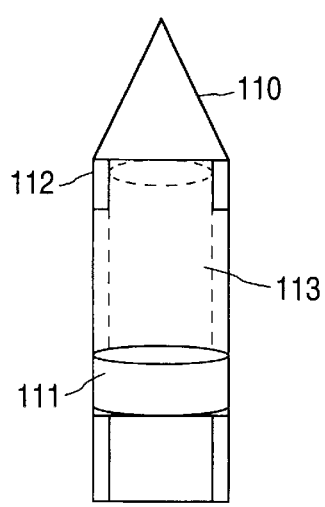
FIG. 8A shows an embodiment of the expulsion end of the injector in the positioning and delivery system, with a sharpened exit point; and, FIG. 8B shows an embodiment of the expulsion end of the injector in the positioning and delivery system, with a beveled hollow point.
Figure 8B:
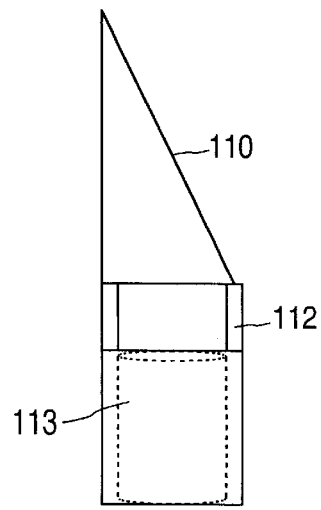

FIGS. 8A and 8B show an embodiment of the expulsion end of the injector. FIG. 8A shows the sharpened end 110 of the hollow tubular shaft or cannula. This view and FIG. 8B also show a plunger 111; a plunger stop 112 and the material or implant to be injected 113. The sharpened end of the tubular shaft can be a beveled hollow point, a solid point with a side exit port near the tip, a hollow sharpened point. The tip can also include a retractable tip cover to prevent tissue from entering the hollow tubular shaft prior to injection of the material.

In a method of the invention the implant is delivered to the tissue to be augmented with a positioning and delivery system. The implant would then stabilize via fibrous tissue in-growth through the lumen and/or tube slits of the tubular segments in soft tissue after the positioning and delivery system is withdrawn. In this embodiment the material will be delivered under cystoscopic observation for periurethral implantation. The incision may be made through the perineum or vaginal wall.

Another embodiment comprises the transurethral insertion of the bulking material via injection under cystoscopic control. In this embodiment the injector is essentially parallel to the cystoscope and the injection is made through the wall of the urethra. The incision can also potentially be made transvaginally.

The methods of the invention can be practiced so as to position the implant either transurethrally through a cystoscope or by puncture (via the perineum or vagina) and suburethral implantation under cystoscopic control.

Thus, in its most basic form the positioning and delivery system comprises a viewing instrument such as a cystoscope, an injector which is adapted to hold and deliver the material to be implanted and a housing with a cavity to closely hold the viewing instrument and a plurality of cavities to closely hold the injector in various positions. Therefore the injector is held at an adjustable angle to the viewing instrument, allowing for accurate and repeatable delivery of the implant or other material.

Ideally the housing in the positioning and delivery system holds the viewing instrument and the injector in such a way that not only the angle between them is adjustable but also the distance between them. The angle is adjustable as the injector can be inserted into different through cavities, each of which specifies a particular angulation. Additionally the entire injector can be rotated relative to the axis of the cystoscope. This can be seen most clearly in FIG. 7B where cavities 103 are available for the injector 101 to be inserted through the housing 100. The viewing instrument and injector are also moveable in the direction of their length between at least two positions and preferably more. As a result accurate and variable positioning of the injected material is possible while still keeping the injector and viewing instrument steady to enable placement of material.

In an especially preferred form, the injector of the positioning and delivery system is a hydraulic injector. A hydraulic injection system increases the amount of pressure that can be applied. The hydraulic injector, which is seen in FIG. 5, comprises a relatively narrow tubular shaft or cannula 83 with an expulsion end and an opposite end, which remains outside the body. The tubular shaft 83 is adapted to contain and deliver the bulking or other material to be delivered into the body 89. The hydraulic injector also comprises a syringe 84 filled with a hydraulic fluid such as saline solution. A luer lock 87 is located between the hydraulic fluid and the tubular shaft 83 to prevent leakage of the fluid into the tubular shaft 83. A plunger 85 is located in the tubular shaft between the luer lock and the material to be delivered into the body. This plunger 85 and the luer lock 87 reduce the danger of the hydraulic fluid leaking into the anatomy. When pressure is applied to the syringe 84 the plunger 85 forces the material out of the expulsion end of the tubular shaft 83. A plunger stop 86 is located within the tubular shaft 83 toward the expulsion end of the tubular shaft 83. The plunger stop 86 is shaped to allow the material to be delivered into the body 89 to pass through to the expulsion end of the tubular shaft 83 while stopping the plunger 85 from passing through to the expulsion end of the tubular shaft. Other forms of injector are available in the art and would be compatible with the positioning and delivery system.

The invention can also be embodied as a method of placing a bulking implant for treating urinary incontinence. In one form the method comprises:

i) selecting an injector through cavity and angle in the positioning and delivery system through which to insert the injector;

ii) inserting the viewing instrument into the urethra of the person undergoing treatment;

iii) making an incision in the periurethral tissue, potentially using the expulsion end of the injector;

iv) accurately positioning the expulsion end of the injector using the viewing instrument;

v) applying pressure to the syringe such that the bulking implant is delivered into the periurethral tissue. The expulsion end of the injector and the distal end of the viewing instrument may then be removed from the urethra. The process may be repeated as necessary to provide sufficient bulking by performing multiple injections with the assembly in fixed position or at a new site.

The method may include the use of a dilator such as a balloon catheter to create a cavity in the expulsion area for better placement of bulking material.

Benefits of the novel positioning and delivery system include the ease and accuracy with which placement and delivery can be performed. The various cavities through which the injector can be positioned and the angular adjustment allow for a variable angle. The position of the injector and viewing instrument can also be varied longitudinally while stability is maintained. In addition, with a sharpened tip on the injector there is no need to have a separate cutting implement to make the necessary incisions and therefore no need to remove the cutting implement in order to deliver the bulking material, although this could be performed as well.

While the invention is directed toward cystourethoscopy and even more particularly to injection of bulking implants the method of delivery can be used for other materials or procedures. Specifically the positioning and delivery system can be used for the delivery of other already known bulking materials, which are used to treat urinary incontinence. These include non-absorbable pyrolytic carbon coated beads suspended in solution (Durasphere brand Advanced Uroscience, St Paul, Minn.), bovine or human collagen (e.g. Contigen brand Collagen/IMPRA/Bard), e-PTFE, temperature sensitive polymers (liquid to hydrogel transition polymers such as from Protein Polymer Technologies, San Diego, Calif.), liquid filled balloons (Uro Vive brand from American Medical Systems, Minnetonka, Minn.), solutions containing genetic material which may cause local tissue growth.

Another method of inserting such bulking materials into the anatomy involves creating a pocket in the periurethral tissue by firstly making an incision in the periurethral tissue then inserting a balloon catheter into the incision. The balloon catheter would then be filled with a fluid such as saline solution or a gas. When the fluid or gas was removed from the balloon catheter and the balloon catheter was removed from the incision a pocket would exist in the periurethral tissue. The next step would be inserting bulking material into the pocket.

The same positioning and delivery system described in this specification can be used to deliver other therapeutic and diagnostic materials. Furthermore, it can be used to remove tissue and perform other similar surgeries.

We claim:

1. A system for accurate positioning and delivery of materials in vivo, the system comprising:

an injector having an expulsion end and an opposite end;

a viewing instrument having a distal end; and a housing, the housing including a through cavity adapted to hold the viewing instrument; the housing further including at least one injector through cavity adapted to hold the injector at an angle to the viewing instrument such that the angle between the viewing instrument and the injector is adjustable, wherein the expulsion end of the injector is positioned proximate to the distal end of the viewing instrument.

2. The system of claim 1, wherein there is a plurality of injector through cavities, each injector through cavity resulting in a different range of available angles between the injector and the viewing instrument.

3. The system of claim 1, wherein the viewing instrument is a cystoscope.

4. The system of claim 1, wherein the injector is adapted to hold and deliver solid or semi-solid bulking materials.

5. The system of claim 1, wherein the injector comprises a hydraulic injection system including:

a relatively narrow tubular shaft or cannula having an expulsion end, the tubular shaft being adapted to contain the material to be delivered into the body;

a syringe filled with a hydraulic fluid;

a luer lock located between the hydraulic fluid and the tubular shaft;

a plunger located in the tubular shaft between the luer lock and the material to be delivered into the body; and, a plunger stop located within the tubular shaft toward the expulsion end of the tubular shaft and shaped to allow the material to be delivered into the body to pass through to the expulsion end of the tubular shaft while stopping the plunger from passing through to the expulsion end of the tubular shaft.

6. The system of claim 5, wherein the hydraulic fluid is saline solution.

7. The system of claim 1, wherein the injector has a hollow beveled point at the expulsion end.

8. The system of claim 1, wherein the injector has a hollow sharpened point at the expulsion end.

9. The system of claim 8, wherein the hollow sharpened point has a side exit port.

10. The system of claim 1, wherein the viewing instrument is moveable longitudinally.

11. The system of claim 1, wherein the injector is moveable longitudinally.

12. The system of claim 1, wherein the viewing instrument and the injector are moveable longitudinally.

13. The system of claim 1, the housing further including an adjustment mechanism for adjusting the distance between the injector and the viewing instrument.

14. The system of claim 13, wherein the adjustment mechanism includes a rotatable knob.

15. A system for accurate positioning and delivery of materials in vivo, the system comprising, an injector having an expulsion end and an opposite end;

a cystoscope having a proximal end which remains outside the body, and a distal end; and, a housing, the housing including a through cavity adapted to hold the cystoscope, the housing further including a plurality of injector through cavities with adjustable angles, each injector through cavity being adapted to hold the injector at an angle to the cystoscope, each injector through cavity resulting in a different range of angles between the injector and the cystoscope;

the expulsion end of the injector being positioned proximate to the distal end of cystoscope;

wherein the viewing instrument and the injector are moveable longitudinally.

16. The system of claim 15, the housing further including an adjustment mechanism for adjusting the distance between the injector and the viewing instrument.

17. The system of claim 16, wherein the adjustment mechanism includes a rotatable knob.

* * * * *